United States Patent [19]

Fiala

[11] Patent Number: Plant 6,672

[45] Date of Patent: Mar. 14, 1989

[54] FLOWERING CRAB APPLE TREE NAMED MAZAM

[75] Inventor: John L. Fiala, Medina, Ohio

[73] Assignee: New Plants, Perry, Ohio

[21] Appl. No.: 129,402

[22] Filed: Dec. 3, 1987

Related U.S. Application Data

[63] Continuation of Ser. No. 895,800, Aug. 12, 1986.

[51] Int. Cl.[4] ..... A01H 5/00

[52] U.S. Cl. ..... Plt./34

[58] Field of Search ..... Plt./34

*Primary Examiner*—Robert E. Bagwill

*Attorney, Agent, or Firm*—Watts, Hoffmann, Fisher & Heinke Co.

[57] ABSTRACT

The present invention relates to a new and distinct variety of flowering crab apple, which was discovered by Father John Fiala as one of a group of unnamed seedling hybrids on my cultivated property, at Medina, Ohio. More particularly, the present invention relates to a novel cultivar of Malus derived from a series of multiple undefined crosses of unnamed Malus seedling hybrids, having unusual and distinctive characteristics, now available as "Madonna", a trademarked plant of Lake County Nursery, Inc., Perry, Ohio.

1 Drawing Sheet

This is a continuation of co-pending plant patent application Ser. No. 895,800, filed on Aug. 12, 1986.

DESCRIPTION

The present invention relates to a new and distinct variety of flowering crab apple tree, Malus, 'Mazam'. This variety was produced by a series of multiple undefined crosses of unnamed Malus seedlings hybrids. The hydridization of this 1965 cross was done by Father John Fiala at his home, 7359 Branch Road, Medina, Ohio. Medina, Ohio is in Zone 4.

This selection has extremely ornamental flowers, a uniquely long period of bud effectiveness, and a dense upright structure. This combination readily distinguishes it from other varieties of the genus.

The accompanying drawings show typical specimens of the flowers, foliage, and branching habit of my new crab apple variety as depicted in color as nearly true as it is reasonably possible to make the same in a photographic illustration of this character. The color terminology is in reference to the Munsell Book of Color 1950, hereinafter referred to as "Munsell".

Referring now more particularly to the drawings.

Figure 1:
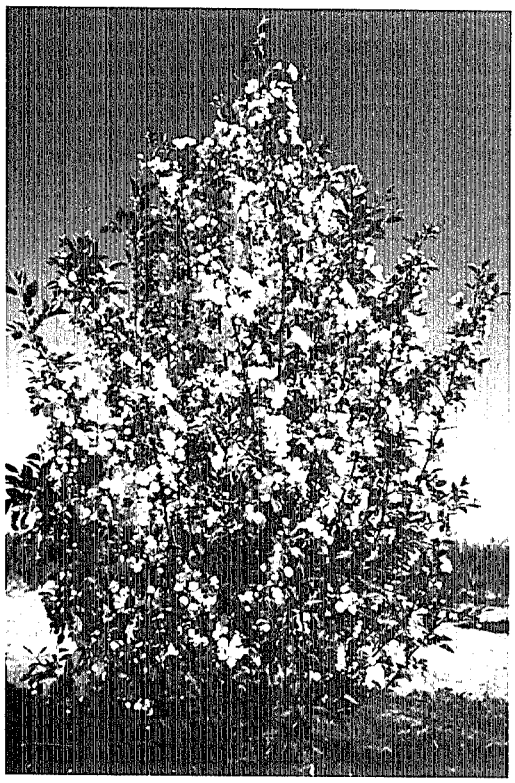
FIG. 1 shows my new flowering crab apple tree with flower in spring blooming season.
Figure 2:
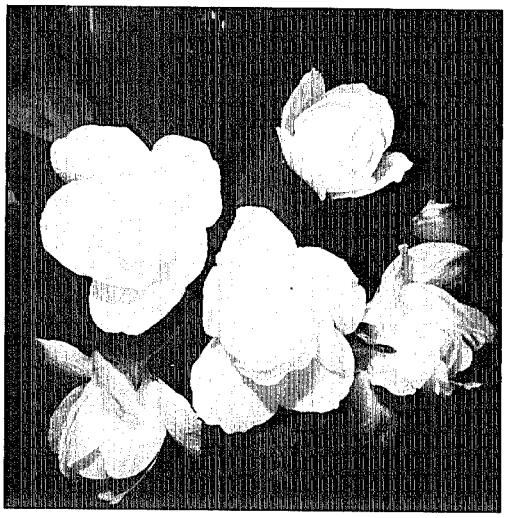
FIG. 2 shows a branchlet of such tree illustrating the flower thereof.
Figure 3:
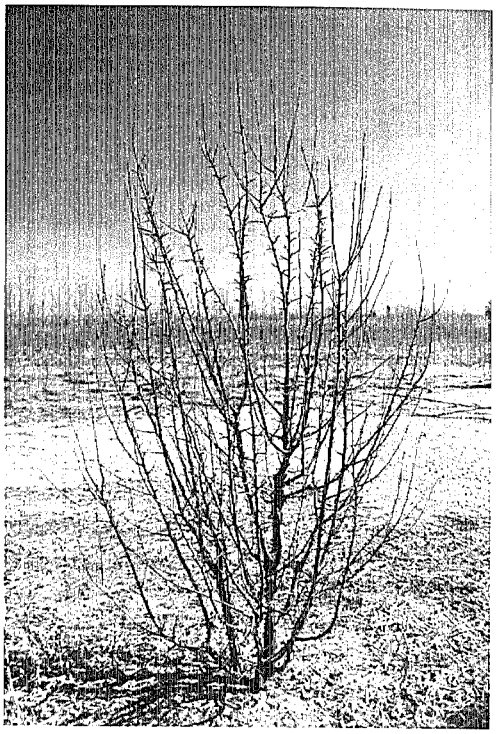
FIG. 3 shows the dormant tree illustrating the dense upright branching habit.

The flowers of this selection are white with a pink (Munsell N9.510) (Munsell 10R912) blush in bud and snowy white (Munsell N9.510) when fully expanded. The buds retain their bright color throughout their long period of effectiveness, which ranges from mid-April through mid-May, when they open. The flowers are pure white (Munsell N9.510) and double, lightly scented, and extremely numerous. The dark green (Munsell 7.56Y416) leaves are advanced at flowering time because of the extended bud stage.

Strong upright growth and a dense branching habit also attracted initial attention to this selection. In normal seasons and sites a growth increment of 18 inches per year has been observed. The multiple-stem crown develops a densley upright form. The tree is presently 8 feet tall, 4 feet wide, and has a caliper of 3 inches at grade. If grown on its own roots it is expected to reach a height approximately 18 feet at maturity, and a width of 10 feet.

New growth during summer months has a relatively bronze color compared with other Malus varieties. The fruit is persistent and undergoes normal color changes through autumn and winter. The immature fruit starts out bright green with a red blush, and turns golden-orange before it gives way to a deep maroon by late November. The color changes to black as the fruit withers during the winter.

Common means of propagation involves budding onto *Malus domestica* understocks. Propagation by softwood cuttings has proven 75% successful. A further horticultural advantage is the ease of transplanting in comparison to other crab apple trees.

The vegetative and reproductive parts of this variety are, in most respects, typical of the genus. The alternate, simple, elliptic leaves are dark green above and paler below. The cuneate leaf base ends in a cuspidate leaf tip. Leaf margins are gently serrulate, elongating slightly near the base. Bronze leaf blades unfold covered with white pubescence, gradually becoming dark green and glabrous with maturity. Leaves of vegetative shoots reach 5 inches in length, of which about $1\frac{1}{4}$ inch represents the maroon-colored petiole. Leaves of fruiting shoots are variably smaller in all dimensions. Fruiting spurs average $\frac{7}{8}$ to 1 inch in length. Immature twigs are maroon and glabrous with small orange lenticels which persist with age. Year-old twigs are a light chocolate brown, occasionally with a burgundy cast, and moderately pruinose. Winter buds are chocolate brown and generally glabrous, often with white hairs on the margins.

The flowers are generally typical, but exaggerated, for the genus. Lightly fragrant, they are normally borne in 6 umbellate clusters. The slender pedicels are $1\frac{1}{4}$ inches long and arise from fruiting spurs about $\frac{7}{8}$ to 1 inch long. Averaging $2\frac{3}{4}$ inches across, the fully expanded, snow-white (Munsell N9.510) corolla normally consists of 15 broadly spatulate petals. These narrow abruptly to slender claws about $\frac{1}{4}$ inch long. The margin of each petal is slightly wavy and, while the tips of the outer petals are reflexed, the inner ones remain slightly inflexed. The slender, acute calyx lobes are reflexed.

The persistant fruit is a small broadened pome containing 5 to 8 single- or double-seeded locules. The fruit averages a little more than $\frac{3}{8}$ inch long and $\frac{1}{2}$ inch in diameter. As it matures it acquires a faint waxy bloom and becomes sparsely flecked with minute rust-colored glands. The stamens and calyx persist; the calyx large and stellate, and the stamens up to $\frac{1}{4}$ inch in length.

I claim:

1. A new and distinct variety of flowering Malus, (crab apple tree), substantially as herein shown and described, characterized particularly by extremely ornamental flowers, a uniquely long period of bud effectiveness, and a dense, upright structure.

* * * * *